US008670998B2

(12) United States Patent
Bertha et al.

(10) Patent No.: US 8,670,998 B2
(45) Date of Patent: Mar. 11, 2014

(54) NOTIFICATION SERVICES FOR PATIENTS

(75) Inventors: Brian Bertha, Danville, CA (US);
Darren O'Neill, San Francisco, CA (US); Stan Kachnowski, Tarrytown, NY (US); Margaret Griffin, New York, NY (US); Cole Manship, New York, NY (US)

(73) Assignee: McKesson Specialty Arizona Inc.

( * ) Notice: Subject to any disclaimer, the term of this patent is extended or adjusted under 35 U.S.C. 154(b) by 115 days.

(21) Appl. No.: 13/309,676

(22) Filed: Dec. 2, 2011

(65) Prior Publication Data

US 2013/0144637 A1     Jun. 6, 2013

(51) Int. Cl.
*G06Q 50/24*     (2012.01)

(52) U.S. Cl.
USPC .............................................. 705/3

(58) Field of Classification Search
USPC .............................................. 705/2–3
See application file for complete search history.

(56) References Cited

U.S. PATENT DOCUMENTS

| | | | |
|---|---|---|---|
| 6,151,586 A * | 11/2000 | Brown | 705/3 |
| 6,327,570 B1 | 12/2001 | Stevens | |
| 6,801,916 B2 | 10/2004 | Roberge et al. | |
| 6,824,052 B2 | 11/2004 | Walsh | |
| 6,850,252 B1 | 2/2005 | Hoffberg | |
| 6,988,075 B1 | 1/2006 | Hacker | |
| 7,034,691 B1 | 4/2006 | Rapaport et al. | |
| 7,155,447 B2 | 12/2006 | Roberge et al. | |
| 7,225,408 B2 | 5/2007 | O'Rourke | |
| 7,248,688 B2 | 7/2007 | Wellons et al. | |
| 7,298,836 B2 | 11/2007 | Wellons et al. | |
| 7,337,123 B2 | 2/2008 | Dvorak et al. | |
| 7,395,216 B2 | 7/2008 | Rosenfeld et al. | |
| 7,436,311 B2 | 10/2008 | Rapaport et al. | |
| 7,490,048 B2 | 2/2009 | Joao | |
| 7,516,103 B1 | 4/2009 | Peitrucha et al. | |
| 7,529,685 B2 | 5/2009 | Davies et al. | |
| 7,533,030 B2 | 5/2009 | Hasan et al. | |
| 7,542,379 B2 | 6/2009 | Kimel et al. | |
| 7,593,549 B2 | 9/2009 | Reiner | |
| 7,652,573 B2 | 1/2010 | Donat et al. | |
| 7,653,634 B2 | 1/2010 | Mathur | |
| 7,679,522 B2 | 3/2010 | Carpenter | |
| 7,685,005 B2 | 3/2010 | Riff et al. | |
| 7,689,438 B1 | 3/2010 | Rappaport et al. | |
| 7,689,441 B1 | 3/2010 | Craft | |
| 7,693,730 B2 | 4/2010 | Hasan et al. | |
| 7,702,524 B1 | 4/2010 | Whibbs et al. | |
| 7,707,047 B2 | 4/2010 | Hasan et al. | |
| 7,714,723 B2 | 5/2010 | Fowler et al. | |
| 7,716,072 B1 | 5/2010 | Green, Jr. et al. | |
| 7,725,842 B2 | 5/2010 | Bronkema | |
| 7,733,224 B2 | 6/2010 | Tran | |

(Continued)

OTHER PUBLICATIONS

"FCC Pens Voluntary Agreement for Wireless Industry to Permit Mobile Phone Unlocking," Bloomberg BNA, Dec. 2013.*

(Continued)

*Primary Examiner* — Michael Fuelling
(74) *Attorney, Agent, or Firm* — Alston & Bird LLP

(57) ABSTRACT

Systems, methods, apparatus, and computer program products are provided for providing at least one notification to a patient. In one embodiment, health-related data/information may be used to identify a patient that satisfies one or more business rules. Notifications to the patient's mobile device can then be provided based on location data.

9 Claims, 6 Drawing Sheets

(56) References Cited

U.S. PATENT DOCUMENTS

| | | | |
|---|---|---|---|
| 7,734,483 B1 | 6/2010 | Smith et al. | |
| 7,740,612 B2 | 6/2010 | Hochman | |
| 7,741,808 B2 | 6/2010 | Fowler et al. | |
| 7,747,644 B1 | 6/2010 | Reihl et al. | |
| 7,756,728 B2 | 7/2010 | Maughan et al. | |
| 7,762,458 B2 | 7/2010 | Stawar et al. | |
| 7,770,524 B1 | 8/2010 | Wa | |
| 7,782,194 B2 | 8/2010 | Stawar et al. | |
| 7,813,822 B1 | 10/2010 | Hoffberg | |
| 7,818,183 B2 | 10/2010 | Schoenberg | |
| 7,831,444 B2 | 11/2010 | Brown et al. | |
| 7,835,928 B2 | 11/2010 | Schoenberg | |
| 7,840,418 B2 | 11/2010 | Schoenberg | |
| 7,840,420 B2 | 11/2010 | Brown | |
| 7,848,937 B2 | 12/2010 | Schoenberg | |
| 7,853,456 B2 | 12/2010 | Soto et al. | |
| 7,912,737 B2 | 3/2011 | Schoenberg | |
| 7,916,014 B2 | 3/2011 | Rapaport et al. | |
| 7,953,613 B2 | 5/2011 | Gizewski | |
| 7,953,699 B2 | 5/2011 | Mathur | |
| 7,974,714 B2 | 7/2011 | Hoffberg | |
| 7,974,924 B2 | 7/2011 | Holla et al. | |
| 7,978,062 B2 | 7/2011 | LaLonde et al. | |
| 7,979,294 B2 | 7/2011 | Larsen et al. | |
| 8,005,692 B2* | 8/2011 | Karkanias et al. | 705/3 |
| 8,032,397 B2 | 10/2011 | Lawless | |
| 2001/0027403 A1 | 10/2001 | Peterson et al. | |
| 2006/0212312 A1* | 9/2006 | Fotsch et al. | 705/2 |
| 2008/0208620 A1* | 8/2008 | Karkanias et al. | 705/2 |
| 2008/0215361 A1 | 9/2008 | Nunnari et al. | |
| 2008/0294490 A1 | 11/2008 | Nuhaan et al. | |
| 2009/0138328 A1 | 5/2009 | Higgins et al. | |
| 2010/0285821 A1 | 11/2010 | Smeeding et al. | |
| 2012/0245955 A1* | 9/2012 | Bari et al. | 705/3 |
| 2012/0253831 A1 | 10/2012 | John et al. | |

OTHER PUBLICATIONS

United States Patent and Trademark Office, Office Action for U.S. Appl. No. 13/172,487, Nov. 29, 2012, 12 pages, USA.

United States Patent and Trademark Office, Office Action for U.S. Appl. No. 13/046,023, Feb. 15, 2013, 22 pages, USA.

United States Patent and Trademark Office, Office Action for U.S. Appl. No. 13/172,487, dated Mar. 7, 2013, 9 pages, USA.

United States Patent and Trademark Office, Office Action for U.S. Appl. No. 13/046,023, dated Nov. 5, 2013, 24 pages, USA.

* cited by examiner

NOTIFICATION SERVICES FOR PATIENTS

BACKGROUND

There are a variety of techniques for providing patients with reminders, disease management programs, incentives, encouragement, and/or rebates. Unfortunately, current techniques are not location-based or time-relevant. Thus, there is a need to provide location-based and time-relevant notifications to patients regarding their health and other information.

BRIEF SUMMARY

In general, embodiments of the present invention provide systems, methods, apparatus, and computer program products for providing at least one notification to a patient.

In accordance with one aspect, a method for providing at least one notification to a patient is provided. In one embodiment, the method comprises (1) identifying a patient that satisfies one or more business rules based at least in part on health-related data associated with the patient; (2) determining whether location data associated with the patient satisfies the one or more business rules; and (3) after determining that the location data associated with the patient satisfies the one or more business rules, providing a notification to a mobile device of the patient.

In accordance with another aspect, a computer program product for providing at least one notification to a patient is provided. The computer program product may comprise at least one computer-readable storage medium having computer-readable program code portions stored therein, the computer-readable program code portions comprising executable portions configured to (1) identify a patient that satisfies one or more business rules based at least in part on health-related data associated with the patient; (2) determine whether location data associated with the patient satisfies the one or more business rules; and (3) after determining that the location data associated with the patient satisfies the one or more business rules, provide a notification to a mobile device of the patient.

In accordance with yet another aspect, an apparatus comprising at least one processor and at least one memory including computer program code is provided. In one embodiment, the at least one memory and the computer program code may be configured to, with the processor, cause the apparatus to at least (1) identify a patient that satisfies one or more business rules based at least in part on health-related data associated with the patient; (2) determine whether location data associated with the patient satisfies the one or more business rules; and (3) after determining that the location data associated with the patient satisfies the one or more business rules, provide a notification to a mobile device of the patient.

BRIEF DESCRIPTION OF THE SEVERAL VIEWS OF THE DRAWING(S)

Reference will be made to the accompanying drawings, which are not necessarily drawn to scale, and wherein.

DETAILED DESCRIPTION

Figure 1:
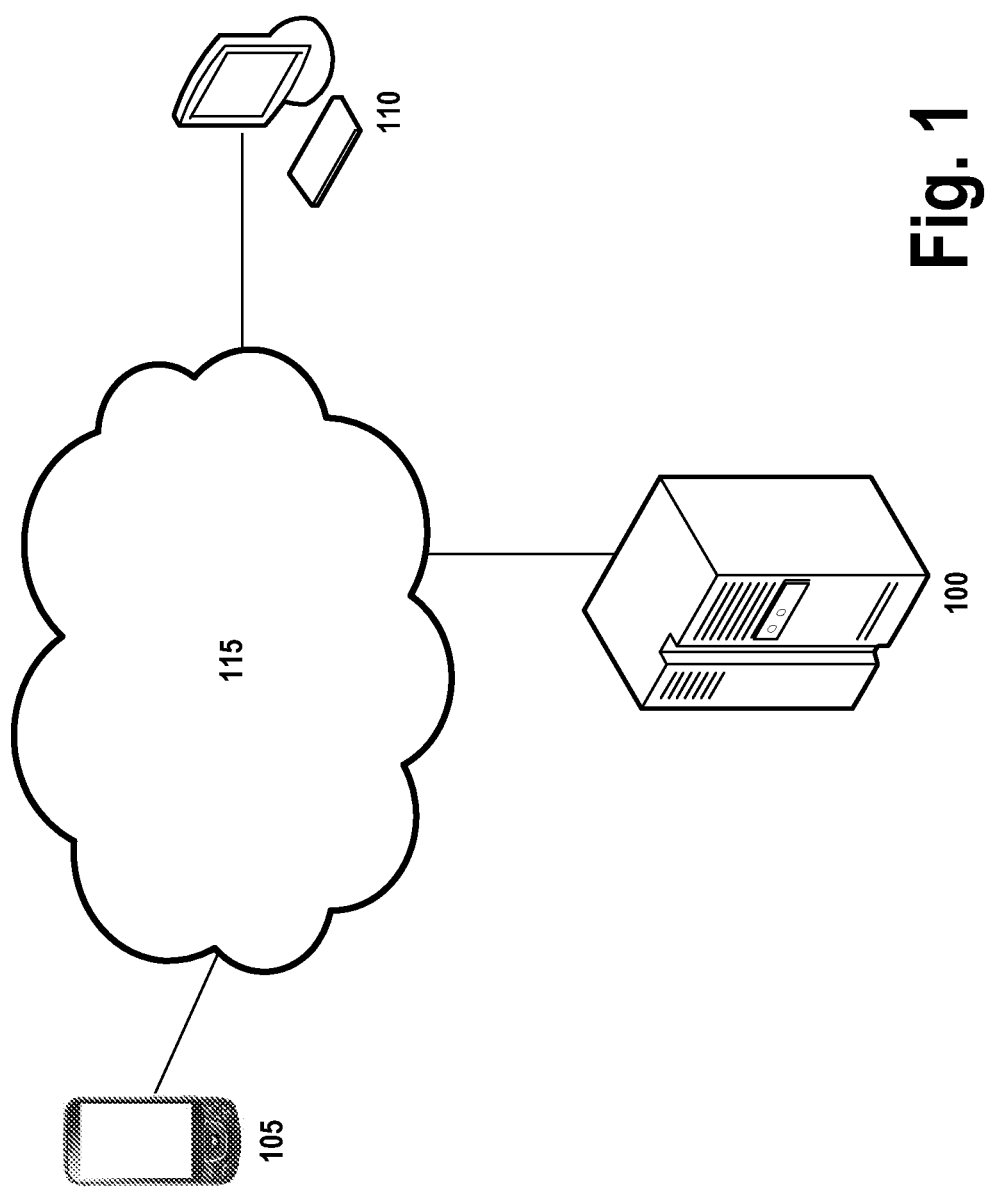
FIG. 1 is a diagram of a system that can be used to practice various embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Methods, Apparatus, Systems, and Computer Program Products

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

II. Exemplary System Architecture

FIG. 1 provides an illustration of a system that can be used in conjunction with various embodiments of the present invention. As shown in FIG. 1, the system may include one or more data management systems 100, one or more mobile devices 105, one or more care provider computing devices 110, and one or more networks 115. Each of the components of the system may be in electronic communication with, for example, one another over the same or different wireless or wired networks including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

1. Exemplary Data Management System

Figure 2:
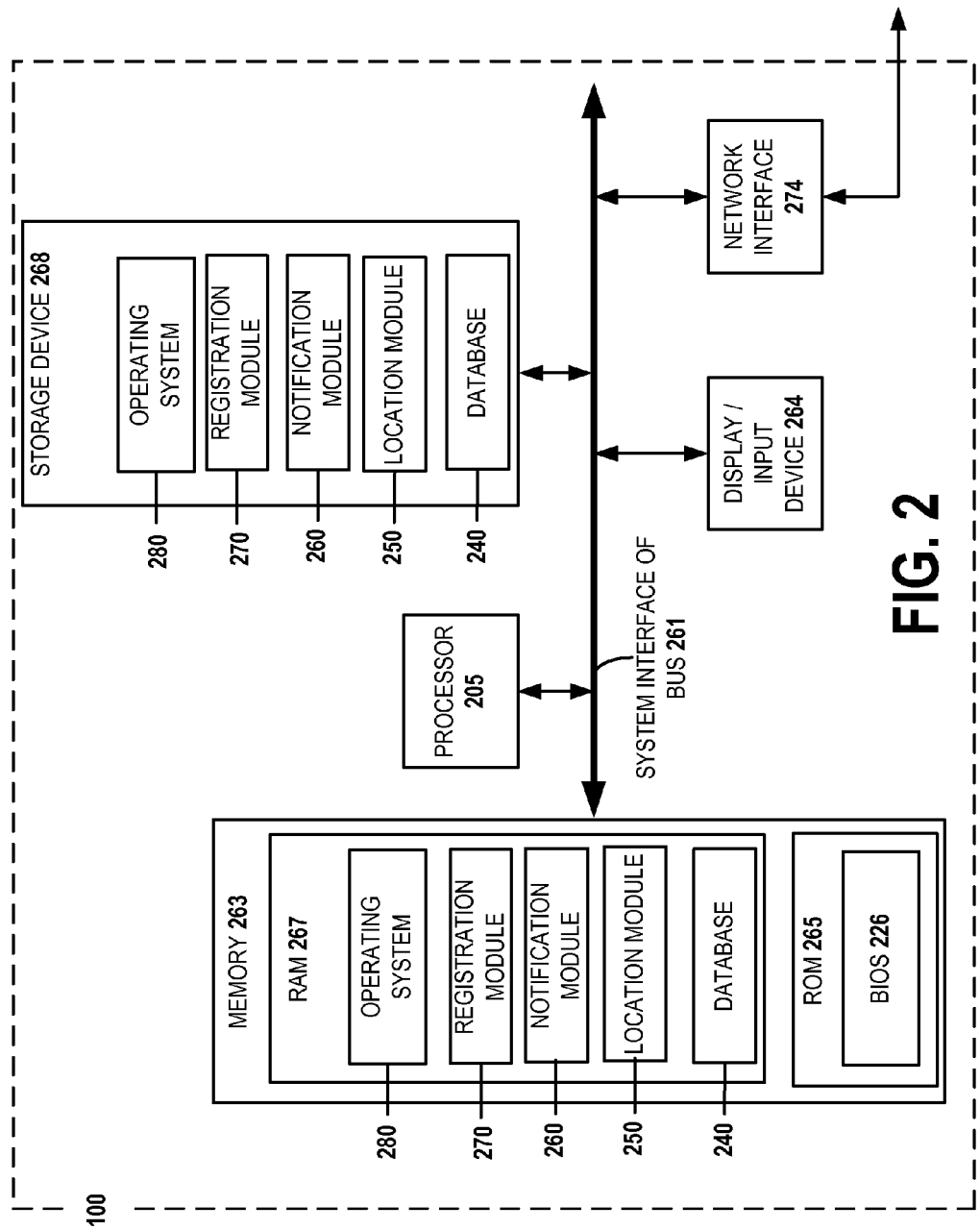
FIG. 2 is a schematic of a data management system that may be used in association with certain embodiments of the present invention.

FIG. 2 provides a schematic of a data management system 100 according to one embodiment of the present invention. In some embodiments, the data management system 100 may be associated with an organization engaged in healthcare-related services. For example, the data management system 100 may be associated with an organization (e.g., care provider or third-party organization) providing various services, such as providing notifications to patients. Further, the data management system 100 may also be capable analyzing health-related data/information, processing healthcare claims, and providing notifications to various devices/entities.

In general, the term "system" may refer to, for example, any computer, computing device, mobile phone, desktop, tablet, notebook or laptop, distributed system, server, blade, gateway, switch, network of computing entities, processing device, or combination of processing devices adapted to perform the functions described herein. As will be understood from this figure, in one embodiment, the data management system 100 includes a processor 205 that communicates with other elements within the data management system 100 via a system interface or bus 261. The processor 205 may be embodied in a number of different ways. For example, the processor 205 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an exemplary embodiment, the processor 205 may be configured to execute instructions stored in memory or otherwise accessible to the processor 205. As such, whether configured by hardware or software methods, or by a combination thereof, the processor 205 may represent an entity capable of performing operations according to embodiments of the present invention when configured accordingly. A display device/input device 264 for receiving and displaying data may also be included in the data management system 100. This display device/input device 264 may be, for example, a keyboard or pointing device that is used in combination with a monitor. The data management system 100 may further include transitory and non-transitory memory 263, which may include both random access memory (RAM) 267 and read only memory (ROM) 265. The data management system's ROM 265 may be used to store a basic input/output system (BIOS) 226 containing the basic routines that help to transfer information to the different elements within the data management system 100.

In addition, in one embodiment, the data management system 100 may include at least one storage device 268, such as a hard disk drive, a CD drive, and/or an optical disk drive for storing information on various computer-readable media. The storage device(s) 268 and its associated computer-readable media may provide nonvolatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. Additionally, each of these storage devices 268 may be connected to the system bus 261 by an appropriate interface.

Furthermore, a number of executable instructions, applications, program modules, and/or the like may be stored by the various storage devices 268 and/or within RAM 267. Such executable instructions, applications, program modules, and/or the like may include an operating system 280, a registration module 270, a notification module 260, and a location module 250. As discussed in more detail below, these executable instructions, applications, program modules, and/or the like may control certain aspects of the operation of the data management system 100 with the assistance of the processor 205 and operating system 280—although their functionality need not be modularized. In addition to the program modules, the data management system 100 may store or be in communication with one or more databases, such as database 240.

Also located within the data management system 100, in one embodiment, is a network interface 274 for interfacing with various computing entities (e.g., with one or more mobile devices 105 and/or care provider computing devices 110). For example, the data management system 100 may be able to receive data/notifications from and transmit data/notifications to the mobile device 105. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data management system 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the data management system's 100 components may be located remotely from other data management system 100 components. Furthermore, one or more of the components may be combined and additional components performing functions described herein may be included in the data management system 100.

2. Exemplary Mobile Device

Figure 3:
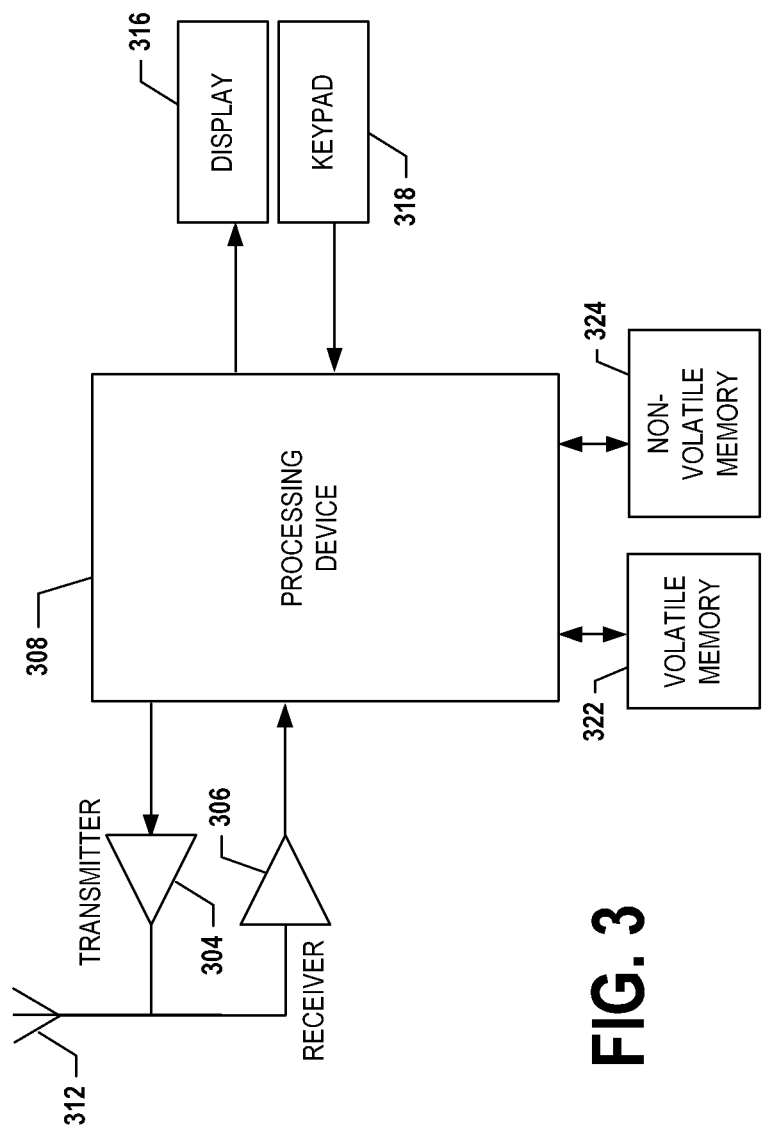
FIG. 3 is a schematic of a mobile device that may be used in association with certain embodiments of the present invention.

FIG. 3 provides an illustrative schematic representative of a mobile device 105 that can be used in conjunction with embodiments of the present invention. In some embodiments, mobile devices 105 may be associated with patients of care providers or patrons of non-care providers. In general, the term "mobile device" may refer to, for example, any computer, computing device, mobile phone, desktop, tablet, notebook or laptop, processing device, or combination of processing devices adapted to perform the functions described herein. For example, as shown in FIG. 3, the mobile device 105 can include an antenna 312, a transmitter 304 (e.g., radio), a receiver 306 (e.g., radio), and a processing device 308 (e.g., a processor, controller, and/or the like) that provides signals to and receives signals from the transmitter 304 and receiver 306, respectively.

The signals provided to and received from the transmitter 304 and the receiver 306, respectively, may include signaling information in accordance with an air interface standard of applicable wireless systems. In this regard, the mobile device 105 may be capable of operating with one or more air interface standards, communication protocols, modulation types, and access types. More particularly, the mobile device 105 may operate in accordance with any of a number of wireless communication standards and protocols, such as those described above with regard to the data management system 100. In a particular embodiment, the mobile device 105 may operate in accordance with multiple wireless communication standards and protocols (e.g., using a Gobi radio), such as GSM, UMTS, 1×RTT, and EVDO, and use multiple wireless carriers (e.g., China Mobile, Vodafone, Telefónica, T-Mobile, Verizon, AT&T, and Qtel). To do so, the mobile device 105 may include integrated mobile reception diversity and integrated power management. Such a configuration can provide for global connectivity to the user.

Via these communication standards and protocols, the mobile device 105 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The mobile device 105 can also download changes, add-ons, and updates, for instance, to its firmware, software (e.g., including modules), and operating system.

According to one embodiment, the mobile device 105 may include a location determining device and/or functionality. For example, the mobile device 105 may include a Global Positioning System (GPS) module adapted to acquire, for example, location data/information (e.g., latitude, longitude, altitude, geocode, course, speed, and/or ephemeris data). In one embodiment, the GPS module may acquire location data/information by identifying the number of satellites in view and the relative positions of those satellites. Additionally or alternatively, triangulation may be used in connection with the mobile device 105 and with various communication points (e.g., cellular towers or Wi-Fi access points) positioned at various locations throughout a geographic area to determine the location of the mobile device 105.

In one embodiment, the mobile device 105 may include, be connected to, or be in communication with an activity monitoring device and/or functionality. For example, such a device or functionality may include a heart rate or pulse monitoring device or functionality, a pedometer, an accelerometer, and/or calorie monitoring device and/or functionality, and/or the like. Via such devices and functionality, the mobile device 105 can be used to monitor a patient's lifestyle and activity levels, such when and how often one exercises. As will be recognized, via such a device and/or functionality, a variety of activities can be monitored and be communicated to various computing devices/entities/systems.

The mobile device 105 may also comprise a user interface (that can include a display 316 coupled to a processing device 308) and/or a user input interface (coupled to the processing device 308). The user input interface can comprise any of a number of devices allowing the mobile device 105 to receive data, such as a keypad 318, a touch display, voice or motion interfaces, or other input device. In embodiments including a keypad 318, the keypad 318 can include the conventional numeric (0-9) and related keys (#, *), and other keys used for operating the mobile device 105 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The mobile device 105 can also include volatile memory 322 and/or non-volatile memory 324, which can be embedded and/or may be removable. For example, the non-volatile memory may be embedded or removable MMCs, secure digital SD memory cards, Memory Sticks, EEPROM, flash memory, hard disk, and/or the like. The memory can store any of a number of pieces or amount of information and data used by the mobile device 105 to implement the functions of the mobile device 105. The memory can also store content, such as computer program code for an application and/or other computer programs.

3. Exemplary Care Provider Computing Device

Care providers may be doctors, hospitals, pharmacies, insurance providers, care managers, and/or other healthcare-related entities or professionals. Care providers may be associated with one or more different care provider computing devices 110 that may be used in connection with embodiments of the present invention. The care provider computing devices 110 may each include one or more components that are functionally similar to those of the data management system 100 and/or mobile device 105. For example, in one embodiment, each of the care provider computing devices 110 may include: (1) a processor that communicates with other elements via a system interface or bus; (2) a display device/input device; (3) transitory and non-transitory memory; and (4) a communications interface. These architectures are provided for exemplary purposes only and are not limiting to the various embodiments. The term "computing device" is used generically to refer to any computer, computing device, mobile phone, desktop, notebook or laptop, distributed system, server, blade, gateway, switch, processing device, or combination of processing devices adapted to perform the functions described herein.

III. Exemplary System Operation

Figure 4:
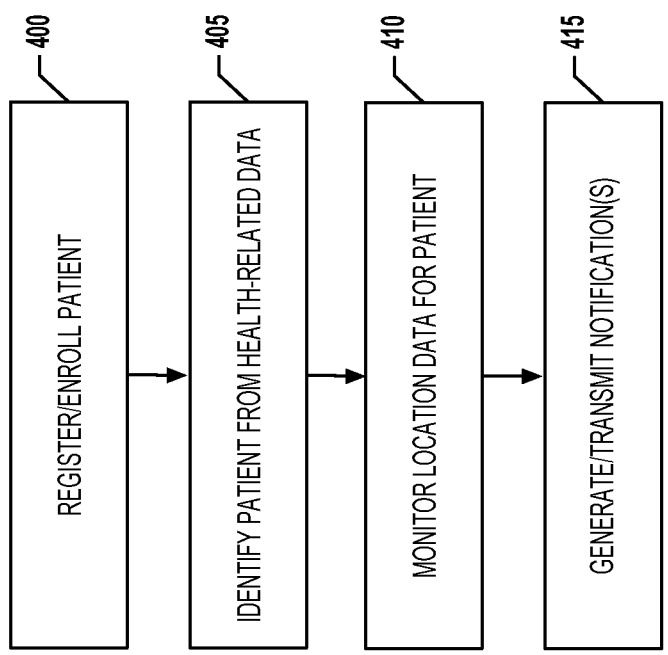
FIG. 4 is a flowchart illustrating operations and processes that can be used in accordance with various embodiments of the present invention.

Reference will now be made to FIGS. 4, 5A, 5B, 5C, 6A, 6B, and 6C. FIG. 4 illustrates operations and processes that can be performed for providing notification services for patients. FIGS. 5A, 5B, 5C, 6A, 6B, and 6C illustrate exemplary input and output produced by various embodiments of the present invention.

1. Registration

In one embodiment, as indicated in Block 400 of FIG. 4, the process may begin with the enrollment/registration for notification services by one or more patients. A patient may be an individual, a family, a company, an organization, an entity, a department within an organization, a representative of an organization and/or person, and/or the like. In one embodiment, a patient (e.g., a patient or patient representative operating a patient computing device) may access a webpage or portal of a care provider to enroll/register for notification services. In another embodiment, a patient may download and install an application for notification services on a mobile device 105. Via the application, the patient may be able to provide communications preferences and view notifications. In yet another embodiment, a care provider (e.g., a care provider or care provider representative operating a care provider computing device 110) may enroll/register patients for notification services. For example, a care provider may enroll/register patients for notification services as a result of the patients requesting such services by filling out a form. Or, a care provider may automatically enroll/register patients for notification services, unless they opt out. As will be recognized, a variety of other techniques and approaches may be used with embodiments of the present invention.

In one embodiment, as part of the enrollment/registration process, a patient may provide biographic information. That is, the patient may provide the patient's name, address (e.g., location data/information), date of birth, medical/customer identification number, health insurance information, Social Security number, and/or the like. By way of example, a patient may provide the following information: (1) Name: John Smith; (2) Address: 6516 Spalding Drive, Norcross, Ga. 30092; (3) Date of Birth: Feb. 19, 1970; (4) Customer Identification Number: BR1254897.1; and/or (5) Social Security number: 534-21-5841.

In one embodiment, a patient may also provide notification preferences. The notification preferences for a patient may identify one or more mobile devices 105 to which notifications can be provided. The notification preferences may also provide patients with the ability to request and receive certain types of notifications. The notification preferences may also identify one or more communication formats for communicating with the patient. The notification formats may include text messages (e.g., Short Message Service (SMS) and/or Multimedia Messaging Service (MMS)), email messages, voice messages, messages viewed using a software application resident on the mobile device 105, and/or a variety of other messages in various communication formats (including social media). In addition to identifying one or more communication formats, a patient can provide the electronic destination addresses (corresponding to the communication formats) to be used in providing notification services to the patient. For instance, for text messages, the patient may provide the phone number associated with one or more mobile devices 105. For email messages, the patient may provide one or more email addresses for email accounts that are accessible via one or more mobile devices 105. For voice messages, the patient may provide one or more phone numbers for which voice messages can be retrieved via one or more mobile devices 105. And for notifications to be viewed using a software application resident on one or more mobile devices 105, the electronic destination addresses may be Internet Protocol (IP) addresses, BlackBerry personal identification numbers, screen names, usernames, International Mobile Subscriber Identity numbers (IMSI), Integrated Circuit Card IDs (IC-CID), Electronic Serial Numbers (ESN), Mobile Equipment Identifiers (MEID), and/or the like.

In one embodiment, based on the biographic information and the notification preferences, the data management system 100 (and/or other computing device) may create a patient profile for each enrolled/registered patient via the enrollment/registration process (e.g., via the registration module 270 of the data management system 100). Or, the data management system 100 (and/or other computing device) may use the biographic information to identify an existing patient profile for a patient and update the profile with the notification preferences. Accordingly, the data management system 100 (and/or other computing device) may create and/or store various patient profiles and notification preferences.

Continuing with the above example, John Smith may provide the following as part of his notification preferences: (1) Email: john.smith@mail.com; (2) Text: (505) 777-7777; and/or (3) Software Application. The data management system 100 (and/or other computing device) may create a patient profile for John Smith or use his biographic information to identify an existing patient profile for him based on, for example, his Social Security Number.

2. Care Provider Locations and Non-Care Provider Locations

In one embodiment, to provide location-based and/or time-relevant notifications to patients, the location of an enrolled/registered patient's mobile device 105 can be monitored. Moreover, the location of an enrolled/registered patient's mobile device 105 can be monitored with regard to one or more care provider locations (e.g., pharmacies, doctor offices, hospitals, pharmacies, etc.) and non-care provider locations (e.g., stores, residences, fitness centers, restaurants, exercise trails, etc.). To do so, a computing device (e.g., data management system 100, mobile device 105, and/or care provider computing device 110) may be used to store latitude, longitude, altitude, geocode, coordinates, and/or position data (e.g., location data/information) for various care provider locations and non-care provider locations. For example, the data management system 100 may store 33.8081412, −84.3933709 (N33° 48.4885', W084° 23.6023') as the coordinates for CVS Caremark Store No. 20821943, which is located at 1943 Peachtree Road Northeast, Atlanta, Ga. 30309. Similarly, the data management system 100 may store 33.9766275, −84.2275741 (or N33° 58.5976', W084° 13.6544') as the coordinates for the Robert D. Fowler YMCA, which is located at 5600 West Jones Bridge Road, Norcross, Ga. 30092. In yet another example, the data management system 100 may store 33.9414158, −84.249209 (or N33° 56.4849', W084° 14.9525') as the coordinates for the Burger King (Store No. 9911) located at 3215 Peachtree Corners Circle, Norcross, Ga. 30092. As will be recognized, such location data/information for any care provider location and/or non-care provider location can be stored by an appropriate computing device. The location data/information can be used by an appropriate computing device to provide notification services.

In one embodiment, in addition to storing location data/information for various locations, a computing device (e.g., data management system 100, mobile device 105, and/or care provider computing device 110) may functionally be able to calculate distances (e.g., in degrees, minutes, seconds, feet, meters, miles, and/or kilometers) from, for example, a patient's mobile device 105 to one or more care provider locations and/or non-care provider locations. With such information, the location of a mobile device 105 can be monitored to determine that a patient has visited a particular location when the mobile device 105 is, for instance, within a predetermined distance (e.g., degrees, minutes, seconds, feet, meters, miles, and/or kilometers) from a care provider location and/or a non-care provider location. For example, assume that John Smith's mobile device 105 indicates that he is at 33.9414160, −84.249210 and that a Burger King (Store No. 9911) is located 33.9414158, −84.249209; based on the distance between the two, a computing device (e.g., data management system 100, mobile device 105, and/or care provider computing device 110) may determine that John stopped by that Burger King. Similarly, via such features, a computing device (e.g., data management system 100, mobile device 105, and/or care provider computing device 110) can determine how often Mr. Smith has visited a fitness location and for how long.

In one embodiment, each location may be associated with a location type, such as fast food location, fitness location, convenient store location, grocer location, and/or the like. For instance, YMCA locations and LA Fitness Center locations may be associated with fitness location types. Similarly, Burger King locations, Chick-fil-A locations, and Pizza Hut locations may be associated with fast food location types. Further, gas stations may be associated with convenience store location types, and grocery stores may be associated with grocer location types. As will be recognized, a variety of other approaches and techniques may be used to adapt to various needs and circumstances.

Additionally or alternatively to storing location data/information, a computing device (e.g., data management system 100, mobile device 105, and/or care provider computing device 110) may be used to define one or more geofences around one or more geographic areas (e.g., one or more care provider locations). In one embodiment, the geofences may be defined to substantially surround various geographic areas, such as substantially surrounding countries, regions, states, counties, cities, towns, interstates, roads, streets, avenues, ways, exit and entrance ramps, shopping centers, buildings, zip codes, neighborhoods, plots of land, care provider locations, non-care provider locations, and/or the like. In one embodiment, geofences may be defined around various care provider locations and non-care provider locations. To do so, the geofences may be defined, for example, by the latitude and longitude coordinates associated with various points along the perimeter of the geographic areas. Alternatively, geofences may be defined based on latitude and longitude coordinates of the center, as well as the radius, of the geographic areas. The geographic areas, and therefore the geofences, may be any shape including, but not limited to, a circle, square, rectangle, an irregular shape, and/or the like. Moreover, the geofenced areas need not be the same shape or size. Accordingly, any combination of shapes and sizes may be used in accordance with embodiments of the present invention. Similarly, a geofence may overlap or reside wholly within another geofence.

By way of example, John Smith may define a two-mile geofence around his primary pharmacy for filling prescriptions (e.g., CVS Caremark Store (Store No. 20821943) located at 1943 Peachtree Road Northeast, Atlanta, Ga. 30309). In another embodiment, care providers and/or non-care providers may define one or more geofences around their respective locations. For example, CVS may define a five-mile geofence around CVS Caremark Store No. 20821943. In another example, a care provider may define one or more geofences around one or more non-care providers, such as United Healthcare defining one or more geofences around the parking lot (or plot of land) of the Robert D. Fowler YMCA located at 5600 West Jones Bridge Road, Norcross, Ga. 30092. Similarly, United Healthcare may define one or more geofences around the parking lot (or plot of land) of Burger King Store No. 9911 (located at 3215 Peachtree Corners Circle, Norcross, Ga. 30092). In these examples, the geofences defined by patients, care providers, and non-care providers may be used to provide notification services. As will be recognized, a variety of other techniques and approaches may be used to define geofences around geographic areas associated with one or more care providers and/or one or more non-care providers (including around a patient's residence).

In one embodiment, once such location data/information has been stored and at least one geofence has been defined, the coordinates (and/or similar methods for defining the geofenced areas) may be stored in a database associated with, for example, a data management system 100, a care provider computing device 110, and/or a mobile device 105 (e.g., via a software application resident on the mobile device 105). Then, as a mobile device's 105 location changes (e.g., by a patient carrying his mobile device 105 with him (or in communication with another device) as he drives, walks, or bikes), a computing device (e.g., data management system 100, mobile device 105, and/or care provider computing device 110) can monitor the mobile device's 105 location with regard to the geofence. For instance, using such location data/information and/or geofences, a computing device (e.g., data management system 100, mobile device 105, and/or care provider computing device 110) may be able to determine when John Smith is at Burger King and how many times he as visited Burger King over a certain period of time. Similarly, via such features, a computing device (e.g., data management system 100, mobile device 105, and/or care provider computing device 110) can determine how often Mr. Smith has visited a fitness location and for how long (and/or when he is at his house).

3. Health-Related Data/Information

In one embodiment, a computing device (e.g., data management system 100, mobile device 105, and/or care provider computing device 110) can receive, access, process, and/or analyze health-related data/information on a routine, periodic, and/or continuous basis. Health-related data/information may include various types of data/information, such as claims data/information, patient data/information, historical data/information, external data/information, and/or weather-related data/information.

In one embodiment, prescriptions may be used to request certain quantities of one or more medications. To assist in processing prescriptions, each prescription may include information, such as the patient's name, address, date of birth, medical/customer identification number, health insurance information, Social Security number, and/or the like. The care provider computing device 110 can process the prescriptions and then transmit claims data/information for the prescriptions to the data management system 100 (and/or other computing device) for processing, storage, and/or payment. Further, with access to claims data/information, the data management system 100 (and/or other computing device) can access, process, and/or analyze the claims data/information for specific indicators, events, factors, and/or triggers in accordance with one or more business rules. For example, the data management system 100 (and/or other computing device) may identify medications that a patient is currently taking (e.g., that a particular patient recently had a prescription filled for Albuterol). The data management system 100 (and/or other computing device) may also identify when a patient switches medications (e.g., a patient switching from Proventil to Volmax). In another example, the data management system 100 (and/or other computing device) may identify patients who have purchased Lipitor or patients residing in zip code 30092 who have purchased Lipitor. In still another example, the data management system 100 (and/or other computing device) may identify geographic areas (e.g., states, counties, cities, towns, zip codes, neighborhoods) associated with an increased number of antiviral prescriptions being filled (e.g., a city or neighborhood in which the number of TAMIFLU prescriptions is above a predetermined threshold within a specific time period). As will be recognized, the data management system 100 (and/or other computing device) may receive, access, process, and/or analyze claims data/information to adapt to a variety of needs and circumstances.

In one embodiment, in addition to claims data/information, the data management system 100 (and other computing devices) may also receive, access, process, and/or analyze other health-related data/information, such as patient data/information and/or historical data/information from an electronic medical record (EMR) of a patient or from other data known about the patient from available sources, or from information provided by patients. This may include data/information regarding treatments, surgeries, schedules, spending habits, activity levels, insurance information, payment information, family history, interests, hobbies, and/or the like. Further, the data management system 100 (and/or other computing device) can access, process, and/or analyze the patient data/information and/or the historical data/information for specific indicators, events, factors, and/or triggers in accordance with one or more business rules. For instance, such analysis may include analyzing the patient data/information and/or the historical data/information longitudinally (e.g., over a period of time). For example, analysis of the patient data/information and/or the historical data/information may indicate a condition (and/or conditions) for which the patient is being treated, such as cancer or diabetes. Similarly, by longitudinally analyzing the patient data/information and/or the historical data/information, the data management system 100 (and/or other computing device) can evaluate how specific medications have been administered over a period of time (e.g., months or years), such as evaluating the prescribed dosage of Lipitor over the past three years. The data management system 100 (and/or other computing device) may also identify particular conditions, programs, and/or treatments from a patient's medical history (e.g., identifying that a patient is currently participating in a smoking cessation program).

In one embodiment, the data management system 100 (and other computing devices) may also receive, access, process, and/or analyze other health-related data/information, such as external data/information from a variety of sources. For instance, environmental factors may have an impact on a patient's health. Thus, external data/information may include weather-related data/information, such as data/information associated with thunderstorms, cold fronts, heat waves, tornados, hurricanes, pollen levels, chilly or damp conditions, precipitation, extreme temperatures, changes in barometric pressure, and/or the like. With access to the weather-related data/information, the data management system 100 (and/or other computing device) can access, process, and/or analyze the weather-related data/information for specific indicators, events, factors, and/or triggers in accordance with one or more business rules. For example, the data management system 100 (and/or other computing device) may identify geographic areas (e.g., states, counties, cities, towns, zip codes, neighborhoods) that may be subject to extreme temperature changes or increased pollen levels (e.g., the pollen level for zip code 30092 is currently above or is expected to be above a predetermined threshold within a specific time period).

In embodiment, external data/information may also include data/information from open source data/information providers, such as the government (e.g., health.data.gov) and/or private entities (e.g., Google). Such data/information may include census data/information, state cancer profile data/information, food recall data/information, product recall data/information, disease outbreak data/information, chemical or toxic exposure data/information, food contamination data/information, food environment atlas data/information, demographic data/information, sales data/information, socio-economic information data/information, vital statistics data/information, and/or the like. With access to such data/information, the data management system 100 (and/or other computing device) can access, process, and/or analyze the data/information for specific indicators, events, factors, and/or triggers in accordance with one or more business rules. For instance, the data management system 100 (and/or other computing device) may identify geographic areas (e.g., states, counties, cities, towns, zip codes, neighborhoods) that may be susceptible to disease outbreak. In another example, the data management system 100 (and/or other computing device) may identify geographic areas (e.g., states, counties, cities, towns, zip codes, neighborhoods) associated with a spike in NyQuil sales (e.g., NyQuil sales for an area has exceeded a predetermined threshold within a specific time period). As will be recognized, the data management system 100 (and/or other computing device) may receive, access, process, and/or analyze various data/information to adapt to a variety of needs and circumstances.

4. Business Rules, Patient Identification, and Notifications

In one embodiment, health-related data/information may be accessed, processed, and/or analyzed for specific indicators, events, factors, and/or triggers in accordance with one or more business rules to identify specific enrolled/registered patients (Block 405 of FIG. 4). As indicated, business rules may be based on a variety of indicators, events, factors, and/or triggers. For instance, business rules may be based on location, gender, medications, activity levels, purchases, zip code, age, income, employer, program participation, disease states, health-related data/information, and/or the like. In one embodiment, certain business rules may require regular, periodic, and/or continuous location monitoring of the identified patients (Block 410 of FIG. 4) to provide location-based and/or time-relevant notifications. In another embodiment, business rules may simply require a location determination (Block 410 of FIG. 4), such as the zip code or city of a patient's primary residential address to provide location-based and/or time-relevant notifications.

Further, as indicated in Block 415 of FIG. 4, the one or more business rules may trigger generating, queuing, and/or providing location-based and/or time-relevant notifications to a mobile device 105 of a patient (e.g., via the notification module 260 of the data management system 100). The notifications may include information for items related to current weather, seasonal, and/or environmental conditions. Additionally or alternatively, the notifications may include information about incentives being offered by a care provider and/or a non-care provider. The notifications may include text, graphics, audio, video, music, images, hyperlinks, codes (e.g., barcodes, Quick Response codes), and/or the like.

Exemplary business rules and exemplary notifications are provided below for understanding embodiments of the present invention. Such examples, however, should not be construed as limiting the various embodiments to the examples provided.

a. Notifications with Location Monitoring

In one embodiment, health-related data/information may be used to trigger (a) monitoring the location (e.g., using location data/information) of a mobile device 105 (and/or any device associated therewith) corresponding to a patient and/or (b) generating, queuing, and/or providing notifications to a mobile device 105 of a patient. To do so, health-related data/information may be accessed, processed, and/or analyzed to identify patients enrolled/registered for notification services that comply with specific business rules. For instance, business rules may be used to identify enrolled/registered patients who recently had prescription filled for Albuterol or Lipitor. Similar, the business rules may be used to identify enrolled/registered patients who have an increased dosage of Lipitor over the past three years or who switched from Proventil to Volmax in the past two months. In one embodiment, patients who have been identified in accordance with business rules may have, for example, their profiles flagged to receive notifications based on their current locations, real-time locations, and/or historical locations in accordance with the business rules.

To do so, the location of one or more mobile devices 105 can be regularly, periodically, and/or continuously monitored (Block 410 of FIG. 4). Monitoring the location of a mobile device 105 (and/or any device associated therewith) may be performed using a variety of techniques and approaches. For example, a mobile device 105 may routinely, periodically, and/or continuously monitor its location via a software application resident on the mobile device 105. With such location data/information, the mobile device 105 (e.g., via a software application resident on the mobile device 105) and/or the data management system 100 can determine when the mobile device 105, for example, is within predetermined distance (e.g., degrees, minutes, seconds, feet, meters, miles, and/or kilometers) from a care provider location and/or a non-care provider location. Similarly, the mobile device 105 can determine when the mobile device 105 (and/or any device associated therewith) enters and/or exits a geofenced area of a care provider location and/or a non-care provider location.

In another example, a mobile device 105 may routinely, periodically, and/or continuously transmit location data/information to the data management system 100 (and/or other computing device). Using the routinely, periodically, and/or continuously received location data/information, the data management system 100 (e.g., via the location module 250) can monitor the mobile device's 105 location and determine when the mobile device 105, for example, is within predetermined distance (e.g., degrees, minutes, seconds, feet, meters, miles, and/or kilometers) from a care provider location and/or a non-care provider location. Similarly, the data management system 100 (e.g., via the location module 250) can determine when the mobile device 105 (or any device associated therewith) enters and/or exits a geofenced area of a care provider location and/or a non-care provider location.

Figure 5C:
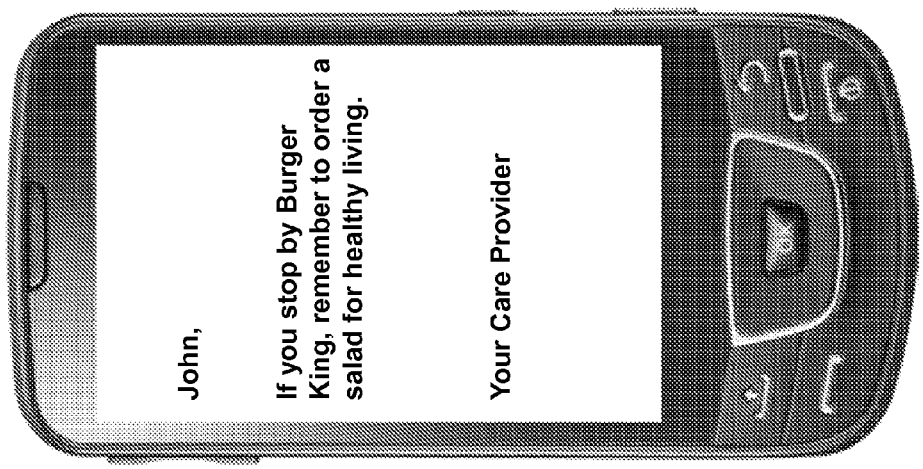
FIGS. 5A, 5B, 5C, 6A, 6B, 6C show exemplary input and output that can be used in accordance with various embodiments of the present invention.
Figure 5B:
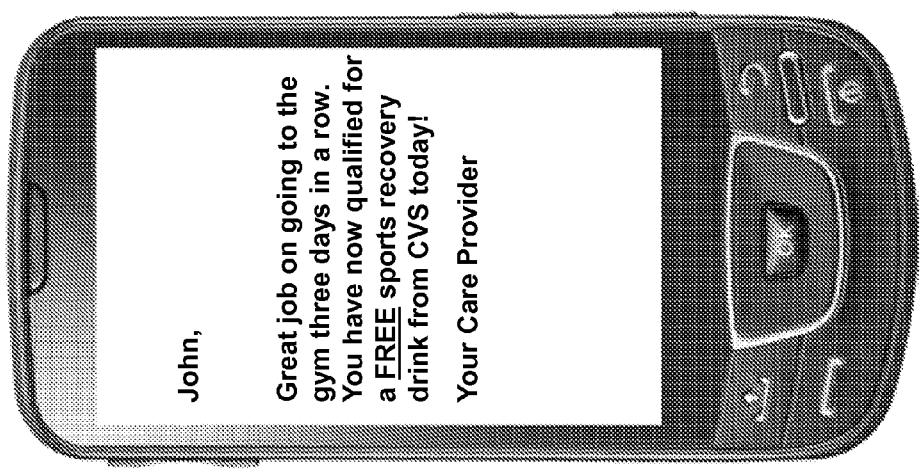
Figure 5A:
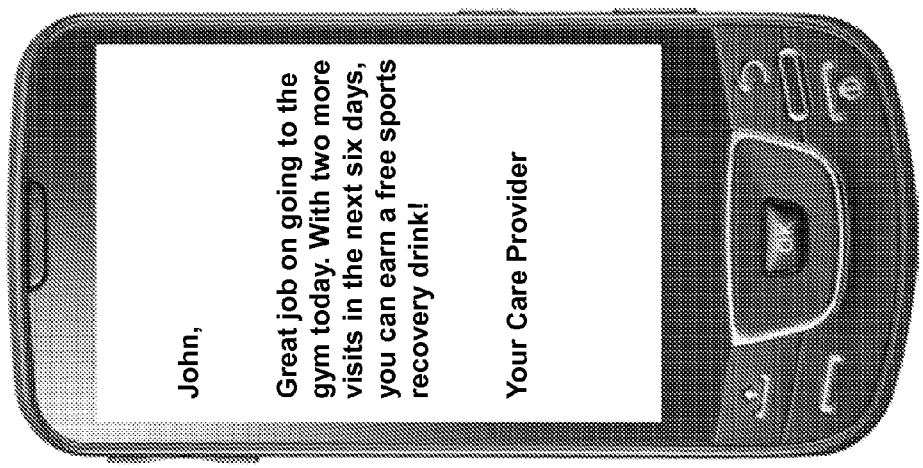

In one embodiment, the location of a mobile device 105 (and/or any device associated therewith) may be used to provide location-based and/or time-relevant notifications to patients in accordance with one or more business rules. For instance, as indicated, one or more business rules may be defined to identify enrolled/registered patients who have had a prescription for Lipitor filled within the past two months. Or, the business rules may be defined to identify enrolled/registered patients who have had an increased dosage of Lipitor over the past three years. For the identified patients, the corresponding business rules may trigger location monitoring to reward and/or incentivize patients for making healthy choices and/or encourage them to make healthier choices. In these two examples, the business rules may require monitoring the location of each patient's mobile device 105 to determine when and how often the identified patients visit fitness locations for periods of time over 30 (e.g., from the patient carrying the mobile device 105 on his person as he drives, walks, or bikes). In response to (e.g., after) a determination by the appropriate computing device that an identified patient (e.g., John Smith) in this example has visited a fitness center (e.g., a fitness location) once in the past seven days or three times in the past seven days, the data management system 100 (and/or other computing device) can generate, queue, and/or provide an appropriate notification to the patient's mobile device 105 (Block 415 of FIG. 4). For example, as shown in FIG. 5A, the notification may read "John, Great job on going to the gym today. With two more visits in the next six days, you can earn a free sports recovery drink! Your Care Provider." In another example shown in FIG. 5B, the notification may read "John, Great job on going to the gym three days in a row. You have now qualified for a FREE sports recovery drink from CVS today! Your Care Provider."

In one embodiment, the above-referenced business rules may also require monitoring the location of each identified patient's mobile device 105 to determine when and how often the identified patients visit fast food locations, such as Burger King. In one embodiment, in response to (e.g., after) a determination by the appropriate computing device that an identified patient (e.g., John Smith) is currently at a fast food location or has visited a fast food location two times in the past seven days, the data management system 100 (and/or other computing device) can generate, queue, and/or provide an appropriate notification to the patient's mobile device 105. For example, as shown in FIG. 5C, the notification may read "John, If you stop by Burger King, remember to order a salad for healthy living. Your Care Provider."

Figure 6C:
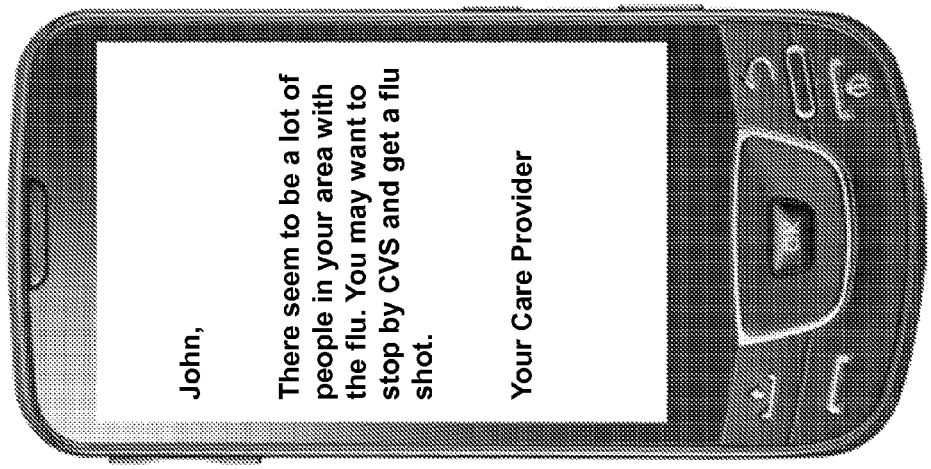
Figure 6B:
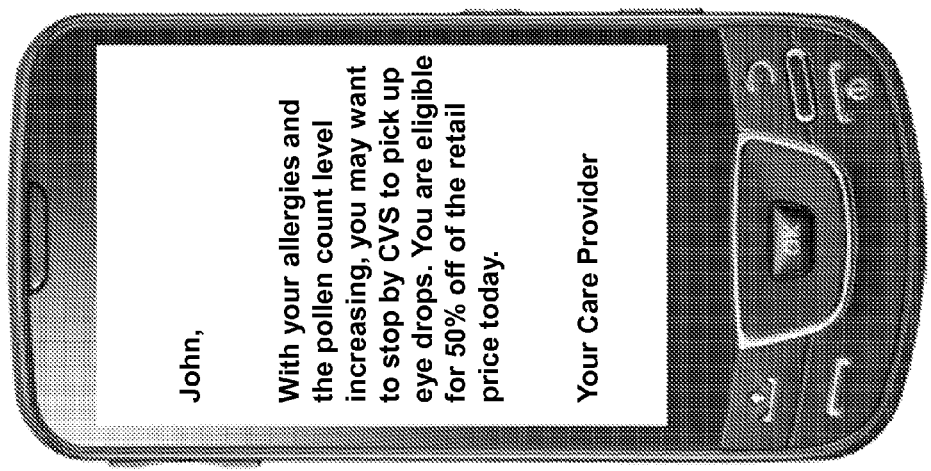
Figure 6A:
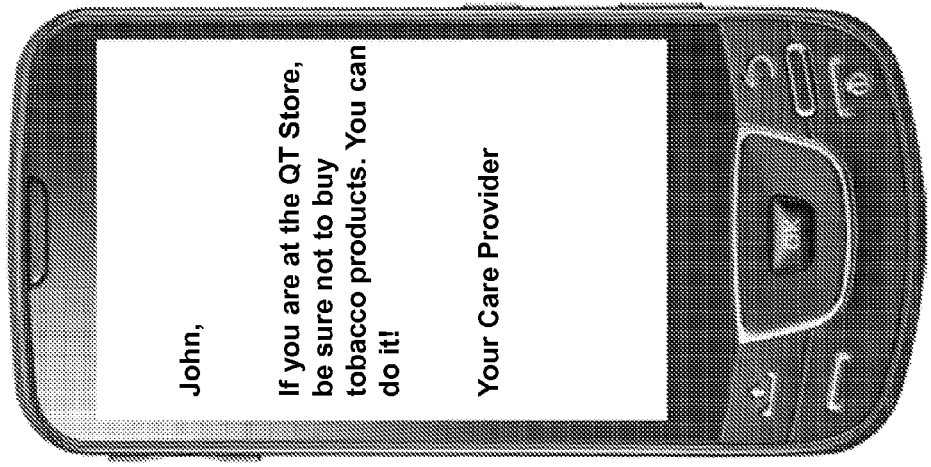

In another example, the business rules may be defined to identify enrolled/registered patients who are currently participating in a smoking cessation program. For the identified patients, the business rules may require location monitoring that can be used to encourage these patients to continuing abstaining from tobacco. In one example, the business rules may require monitoring the location of each patient's mobile device 105 to determine when such patients are at convenience store locations (e.g., as the patient carries the mobile device 105 on his person as he drives, walks, or bikes). In one embodiment, in response to (e.g., after) a determination by the appropriate computing device that an identified patient (e.g., John Smith) is currently at a convenience store location, the data management system 100 (and/or other computing device) can generate, queue, and/or provide an appropriate notification to the patient's mobile device 105 (Block 415 of FIG. 4). For example, as shown in FIG. 6A, the notification may read "John, If you are at the QT Store, be sure not to buy tobacco products. You can do it! Your Care Provider."

In still another example, the business rules may be defined to identify enrolled/registered patients who recently had a prescription filled for Albuterol and who are located in a geographic area with a pollen level above 4.9. For the identified patients, the business rules may require location monitoring to provide an incentive to these patients when they are within a predetermined distance (e.g., two miles) from a specific store, such as CVS Caremark Store No. 20821943. In one embodiment, in response to (e.g., after) a determination by the appropriate computing device that an identified patient (e.g., John Smith) is currently within a predetermined distance (e.g., two miles) from CVS Caremark Store No. 20821943 (e.g., from the patient carrying the mobile device 105 on his person as he drives, walks, or bikes), the data management system 100 (and/or other computing device) can generate, queue, and/or provide an appropriate notification to the patient's mobile device 105 (Block 415 of FIG. 4). For example, as shown in FIG. 6B, the notification may read "John, With your allergies and the pollen count level increasing, you may want to stop by CVS to pick up eye drops. You are eligible for 50% off of the retail price today. Your Care Provider." Such a notification may also include a code (e.g., barcode, Quick Response code) that can be scanned by store employees, for instance, to apply the discount.

In another example, the business rules may be defined to identify enrolled/registered patients who are in a geographic area (e.g., states, counties, cities, towns, zip codes, neighborhoods) associated with a spike in NyQuil sales (e.g., NyQuil sales for an area has exceeded a predetermined threshold within a specific time period). Similarly, the business rules may be defined to identify enrolled/registered patients who are in a geographic area (e.g., states, counties, cities, towns, zip codes, neighborhoods) associated with an increase of antiviral prescriptions being filled (e.g., the number of TAMIFLU prescriptions is above a predetermined threshold within a specific time period). For the identified patients (e.g., John Smith), the business rules may require location monitoring to provide an incentive or reminder to these patients when they are within a predetermined distance (e.g., two miles) from a specific store, such as CVS Caremark Store No. 20821943. In one embodiment, in response to (e.g., after) a determination by the appropriate computing device that an identified patient (e.g., John Smith) is currently within a predetermined distance (e.g., two miles) from CVS Caremark Store No. 20821943, the data management system 100 (and/or other computing device) can generate, queue, and/or provide an appropriate notification to the patient's mobile device 105 (Block 415 of FIG. 4). For example, as shown in FIG. 6C, the notification may read "John, There seem to be a lot of people in your area with the flu. You may want to stop by CVS and get a flu shot. Your Care Provider."

As will be recognized, a variety of other approaches and techniques can be used to provide any number of notifications to patients. Thus, these examples are provided for illustrative purposes and are not limiting to embodiments of the present invention.

b. Notifications with Location Determining/Identification

In one embodiment, health-related data/information may be used to trigger (a) determining the location (e.g., using location data/information) of a patient (e.g., state, county, city, or zip code of a patient's residential address, as indicated Block 410 of FIG. 4) and/or (b) generating, queuing, and/or providing notifications to a mobile device 105 of a patient (Block 415 of FIG. 4). As indicated, to do so, health-related data/information may be accessed, processed, and/or analyzed to identify patients enrolled/registered for notification services that comply with specific business rules.

In one example, the business rules may be defined to identify enrolled/registered patients who recently had a prescription filled for Albuterol and who are located in a geographic area with a pollen level above 4.9. For the identified patients (e.g., John Smith), the data management system 100 (and/or other computing device) can generate, queue, and/or provide an appropriate notification to the patient's mobile device 105 (Block 415 of FIG. 4). For example, as shown in FIG. 6B, the notification may read "John, With your allergies and the pollen count level increasing, you may want to stop by CVS to pick up eye drops. You are eligible for 50% off of the retail price today. Your Care Provider." Such a notification may also include a code (e.g., barcode, Quick Response code) that can be scanned by store employees, for instance, to apply the discount.

In another example, the business rules may be defined to identify enrolled/registered patients who are in a geographic area (e.g., states, counties, cities, towns, zip codes, neighborhoods) associated with a spike in NyQuil sales (e.g., NyQuil sales for an area has exceeded a predetermined threshold within a specific time period). Similarly, the business rules may be defined to identify enrolled/registered patients who are in a geographic area (e.g., states, counties, cities, towns, zip codes, neighborhoods) associated with an increase of antiviral prescriptions being filled (e.g., the number of TAMIFLU prescriptions is above a predetermined threshold within a specific time period). For the identified patients (e.g., John Smith), the data management system 100 (and/or other computing device) can generate, queue, and/or provide an appropriate notification to the patient's mobile device 105 (Block 415 of FIG. 4). For example, as shown in FIG. 6C, the notification may read "John, There seem to be a lot of people in your area with the flu. You may want to stop by CVS and get a flu shot. Your Care Provider."

As will be recognized, embodiments of the present invention can be used to provide various notifications for public health campaigns, to promote healthier lifestyles, to provide incentives, to provide reminders, to provide encouragement, and/or the like.

IV. Conclusion

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for providing at least one notification to a patient, the method comprising:
    for a patient registered for notification services, determining, via one or more processors, whether health-related data associated with the patient satisfies one or more business rules;
    storing, via the one or more processors, notification preferences for the patient that identify at least one communication format and at least one electronic destination address to be used in providing notifications to a mobile device associated with the patient, wherein the at least one communication format is selected from the group consisting of a text message, an email message, and a voice message;
    monitoring, via the one or more processors, the location of the mobile device associated with the patient to determine when the location of the mobile device associated with the patient is within a predetermined distance from a designated location; and
    responsive to determining that the location of the mobile device associated with the patient is within the predetermined distance from the designated location, providing, via the one or more processors, a notification to the mobile device associated with the patient, the notification corresponding to the one or more business rules, the notification preferences, and the designated location.

2. The method of claim 1, wherein the health-related data comprises claims data and external data.

3. The method of claim 1, wherein (a) the notification is an incentive based at least in part on the health-related data and (b) the incentive comprises a discount for purchasing an item.

4. A computer program product for providing at least one notification to a patient, the computer program product comprising at least one non-transitory computer-readable storage medium having computer-readable program code portions stored therein, the computer-readable program code portions comprising:

an executable portion configured to, for a patient registered for notification services, determine whether health-related data associated with the patient satisfies one or more business rules;

an executable portion configured to store notification preferences for the patient that identify at least one communication format and at least one electronic destination address to be used in providing notifications to a mobile device associated with the patient, wherein the at least one communication format is selected from the group consisting of a text message, an email message, and a voice message;

an executable portion configured to monitor location of the mobile device associated with the patient to determine when the location of the mobile device associated with the patient is within a predetermined distance from a designated location; and an executable portion configured to, responsive to determining that the location of the mobile device associated with the patient is within the predetermined distance from the designated location, provide a notification to the mobile device associated with the patient, the notification corresponding to the one or more business rules, the notification preferences, and the designated location.

5. The computer program product of claim 4, wherein the health-related data comprises claims data and external data.

6. The computer program product of claim 4, wherein (a) the notification is an incentive based at least in part on the health-related data and (b) the incentive comprises a discount for purchasing an item.

7. An apparatus comprising at least one processor and at least one memory including computer program code, the at least one memory and the computer program code configured to, with the processor, cause the apparatus to at least:

for a patient registered for notification services, determine whether health-related data associated with the patient satisfies one or more business rules;

store notification preferences for the patient that identify at least one communication format and at least one electronic destination address to be used in providing notifications to a mobile device associated with the patient, wherein the at least one communication format is selected from the group consisting of a text message, an email message, and a voice message;

monitor the location of the mobile device associated with the patient to determine when the location of the mobile device associated with the patient is within a predetermined distance from a designated location; and responsive to determining that the location of the mobile device associated with the patient is within the predetermined distance from the designated location, provide a notification to the mobile device associated with the patient, the notification corresponding to the one or more business rules, the notification preferences, and the designated location.

8. The apparatus of claim 7, wherein the health-related data comprises claims data and external data.

9. The apparatus of claim 7, wherein (a) the notification is an incentive based at least in part on the health-related data and (b) the incentive comprises a discount for purchasing an item.

* * * * *